United States Patent [19]

Rivier et al.

[11] Patent Number: 5,109,111
[45] Date of Patent: Apr. 28, 1992

[54] CRF ANTAGONISTS

[75] Inventors: Jean E. F. Rivier; Wylie W. Vale, Jr.; Catherine L. Rivier, all of La Jolla; Jean-Francois Hernandez, San Diego, all of Calif.

[73] Assignee: The Salk Institute for Biological Studies, San Diego, Calif.

[21] Appl. No.: 498,814

[22] Filed: Mar. 23, 1990

Related U.S. Application Data

[63] Continuation-in-part of Ser. No. 248,917, Sep. 23, 1988, abandoned.

[51] Int. Cl.$^5$ ................................................. C07K 7/38
[52] U.S. Cl. ................................... 530/306; 530/324; 530/334; 530/335; 530/857; 930/20; 930/21; 930/70; 930/DIG. 570; 930/DIG. 572; 930/DIG. 820; 930/DIG. 822; 514/805
[58] Field of Search ............... 530/306, 324, 325, 334, 530/335, 857; 514/12, 15, 805; 930/21, 20, 70, DIG. 570, DIG. 572, DIG. 820, DIG. 822

[56] References Cited

U.S. PATENT DOCUMENTS

| | | | |
|---|---|---|---|
| 3,761,459 | 9/1973 | Pless et al. | 530/324 |
| 3,770,715 | 11/1973 | Tesser et al. | 530/324 |
| 3,792,033 | 2/1974 | Iselin et al. | 530/324 |
| 4,594,329 | 6/1986 | Vale, Jr. et al. | 514/12 |
| 4,605,642 | 8/1986 | Rivier et al. | 514/12 |

OTHER PUBLICATIONS

Britton et al., Brain Research, vol. 369, pp. 303–306, (1986).
Rivier et al., Science, vol. 224, pp. 889–891, (1984).
Acta Endocrinologica, 75 (1974), 24–32, Hulliger et al.
Chem. Abs., 102, 125589e, Yanaihara et al.
Horumon to Rinsho, (1984) 32(11) 1039–1045.
The Merck Manual, eleventh ed., 1966, 1105–1106.

*Primary Examiner*—Lester L. Lee
*Assistant Examiner*—T. D. Wessendorf
*Attorney, Agent, or Firm*—Fitch, Even, Tabin & Flannery

[57] ABSTRACT

Several known members of the corticotropin releasing factor (CRF) family have been synthesized and tested, including human and rat CRF which have the formula: H-Ser-Glu-Glu-Pro-Pro-Ile-Ser-Leu-Asp-Leu-Thr-Phe-His- Leu-Leu-Arg-Glu-Val-Leu-Glu-Met-Ala-Arg-Ala-Glu-Gln- Leu-Ala-Gln-Gln-Ala-His-Ser-Asn-Arg-Lys-Leu-Met-Glu- Ile-Ile-NH$_2$. Peptides are herein disclosed that are potent competitive antagonists of CRF in mammals. One which has been found to be particularly potent is: H-D-Phe-His-Leu-Leu-Arg-Glu-Val-Leu-Glu-Nle-Ala- Arg-Ala-Glu-Gln-Leu-Ala-Gln-Gln-Ala-His-Ser-Asn- Arg-Lys-Leu-Nle-Glu-Ile-Ile-NH$_2$. One that has shown particularly prolonged duration of potency is: H-D-Phe-His-Leu-Leu-Arg-Glu-Val-Leu-Glu-Nle-Ala- Arg-Ala-Glu-Gln-Leu-Ala-Gln-Gln-Ala-His-Ser-Asn- Arg-Lys-CML-Nle-Glu-Ile-Ile-NH$_2$. These antagonists or pharmaceutically or veterinarily acceptable salts thereof, dispersed in a pharmaceutically or veterinarily acceptable liquid or solid carrier, can be administered to mammals, including humans, to achieve a prevent elevation of ACTH, $\beta$-endorphin, $\beta$-lipotropin, other products of the pro-opiomelanocortin gene and corticosterone levels and/or a lowering of brain mediated responses to stress over an extended period of time. They may also be used to affect mood, memory and learning, as well as diagnostically.

6 Claims, No Drawings

5,109,111

CRF ANTAGONISTS

This invention was made with Government support under Grant No. DK-26741 awarded by the National Institutes of Health (DHHS). The Government has certain rights in this invention.

This application is a continuation-in-part of our application Ser. No. 248,917 filed Sept. 23, 1988, now abandoned.

This invention is directed to peptides and to methods for pharmaceutical treatment of mammals using such peptides. More specifically, the invention relates to antagonists of the hentetracontapeptide CRF, to pharmaceutical compositions containing CRF antagonists and to methods of treatment of mammals using CRF antagonists.

BACKGROUND OF THE INVENTION

Experimental and clinical observations have supported the concept that the hypothalamus plays a key role in the regulation of adenohypophysial corticotropic cells secretory functions. Over 25 years ago, Guillemin, Rosenberg and Saffran and Schally independently demonstrated the presence of factors in hypothalamus which would increase the rate of ACTH secretion by the pituitary gland incubated in vitro or maintained in an organ culture. None of the secretagogs characterized met the criteria expected of a physiologic corticotropin releasing factor (CRF) until ovine CRF (oCRF) was characterized in 1981 and, as disclosed in U.S. Pat. No. 4,415,558, was found to have the formula: H-Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-G ln-Ile-Ala-NH$_2$.

Sauvagine is a 40-residue, amidated generally similar peptide which was isolated from the skin of the South American frog Phyllomedusa sauvagei. It was characterized by Erspamer et al. and was described in *Regulatory Peptides*, Vol. 2 (1981), pp. 1-13. Sauvagine has the formula: pGLu-Gly-Pro-Pro-Ile-Ser-Ile-Asp-Leu-Ser-Leu-Glu-Leu-Le u-Arg-Lys-Met-Ile-Glu-Ile-Glu-Lys-Gln-Glu-Lys-Glu-L ys-Gln-Gln-Ala-Ala-Asn-Asn-Arg-Leu-Leu-Leu-Asp-Thr-I le-NH$_2$. Urotensin I is a homologous 41-residue peptide which was isolated from the urophyses of teleost fish as reported in Ichikawa, et al. *Peptides*, 3, 859 (1982). Sauvagine, Urotensin I, and members of the CRF family have been reported to have biological activity in lowering blood pressure in mammals and in stimulating the secretion of ACTH and β-endorphin.

Rat CRF has been characterized as a 41-amino acid peptide having high homology with oCRF and the formula: H-Ser-Glu-Glu-Pro-Pro-Ile-Ser-Leu-Asp-Leu-Thr-Phe-His-L eu-Leu-Arg-Glu-Val-Leu-Glu-Met-Ala-Arg-Ala-Glu-Gln-L eu-Ala-Gln-Gln-Ala-His-Ser-Asn-Arg-Lys-Leu-Met-Glu-I le-Ile-NH$_2$. Human CRF has the same structure, and the abbreviations rCRF and hCRF are used interchangeably.

SUMMARY OF THE INVENTION

Competitive antagonists of the 41-residue CRF family of peptides have been synthesized which have the following formula: Y-R$_9$-R$_{10}$-R$_{11}$-R$_{12}$-R$_{13}$-leu-leu-Arg-R$_{17}$-R$_{18}$-R$_{19}$-R$_{20}$-R$_{21}$-R$_{22}$-R$_{23}$-R$_{24}$-R$_{25}$-R$_{26}$-R$_{27}$-R$_{28}$-R$_{29}$-Gln-Ala-R$_{32}$-R$_{33}$-Asn-Arg-R$_{36}$-R$_{37}$-Nle-R $_{39}$-R$_{40}$-R$_{41}$-NH$_2$ wherein H is an acyl group having 7 or less carbon atoms or hydrogen; R$_9$ is Asp or desR$_9$; R$_{10}$ is Leu or desR$_{10}$; R$_{11}$ is Thr, Ser or desR$_{11}$; R$_{12}$ is (Q)D-Phe, D-Tyr, D-Leu, D-His, D-Nal, D-Pal, D-Ile, D-Nle, D-Val, D-Met, Phe or Leu; Q is H, 4Cl or 4F; R$_{13}$ is His, Tyr or Glu; R$_{17}$ is Glu, Asn or Lys; R$_{18}$ is Val, Nle or Met; R$_{19}$ and R$_{24}$ are selected from the group consisting of leu, Ile, ala, Gly, Val, Nle, Phe, Asn and Gln; R$_{20}$ is Glu or D-Glu; R$_{21}$ is Met, Nva, Ile, ala, leu, Nle, Val, Phe or Gln; R$_{22}$ is ala, Thr, Asp or Glu; R$_{23}$ is Arg, Orn, Har or Lys; R$_{25}$ is Asp or Glu; R$_{26}$ is Gln, Asn or Lys; R$_{27}$ is Ileu, Ile, Nla, Val, Nva, Met, Nle, Phe, Asp, Asn, Gln or Glu; R$_{28}$ is ala, Arg or Lys; R$_{29}$ is Gln or Glu, R$_{32}$ is His, Gly, Tyr or ala; R$_{33}$ is Ser, Asn, leu, Thr or ala; R$_{36}$ is Lys, Orn, Arg, Har or leu; R$_{37}$ is leu or Tyr; R$_{39}$ is Glu or Asp; R$_{40}$ is Ile, Thr, Glu, ala, Val, leu, Nle, Phe, Nva, Gly or Gln; and R$_{41}$ is ala, Ile, Gly, Val, leu, Nle, Phe, Nva or Gln; or a nontoxic addition salt thereof.

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations to identify the alpha-amino acid residues, and where the amino acid residue has isomeric forms, it is the L-form of the amino acid that is represented unless otherwise expressly indicated, e.g. Ser=L-serine, Nle=L-norleucine, Nva=L-norvaline, Har=L-homoarginine, Orn=L-ornithine, etc. In addition the following abbreviations are used: leu=either L-leucine or C$^\alpha$CH$_3$-L-leucine (CML); ala=either L-alanine or C$^\alpha$CH$_3$-L-alanine (CMA); D-Nal=D-alanine, the β-carbon of which is substituted with naphthalene and linked to the 1- or 2-carbon thereon, and D-Pal=D-alanine, the β-carbon of which is linked to the 3-position carbon of pyridine.

Pharmaceutical compositions in accordance with the invention include such CRF antagonists, or nontoxic addition salts thereof, dispersed in a pharmaceutically or veterinarily acceptable liquid or solid carrier. The administration of such peptides or pharmaceutically or veterinarily acceptable addition salts thereof to mammals, particularly humans, in accordance with the invention may be carried out for the regulation of secretion of ACTH, β-endorphin, β-lipotropin, other products of the pro-opiomelanocortin gene and corticosterone and/or for the lowering of stress responses and/or for affecting mood, behavioral metabolic and gastrointestinal functions and autonomic nervous system activities. Furthermore CRF antagonists may be used for the evaluation of the status of pituitary, metabolic, cardiovascular, gastrointestinal or central nervous system functions.

DETAILED DESCRIPTION OF THE PREFERRED EMBODIMENTS

The invention provides antagonists of CRF having the following Formula (I): Y-R$_9$-R$_{10}$-R$_{11}$-R$_{12}$-R$_{13}$-leu-leu-Arg-R$_{17}$-R$_{18}$-R$_{19}$-R$_{20}$-R$_{21}$-R$_{22}$-R$_{23}$-R$_{24}$-R$_{25}$-R$_{26}$-R$_{27}$-R$_{28}$-R$_{29}$-Gln-ala-R$_{32}$-R$_{33}$-Asn-Arg-R$_{36}$-R$_{37}$-Nle-R $_{39}$-R$_{40}$-R$_{41}$-NH$_2$ wherein Y is an acyl group having 7 or less carbon atoms or hydrogen; R$_9$ is Asp or desR$_9$; R$_{10}$ is Leu or desR$_{10}$; R$_{11}$ is Thr, Ser or desR$_{11}$; R$_{12}$ is (Q)D-Phe, D-Tyr, D-Leu, D-His, D-Nal, D-Pal, D-Ile, D-Nle, D-Val, D-Met, Phe or Leu; Q is H, 4Cl or 4F; R$_{13}$ is His, Tyr or Glu; R$_{17}$ is Glu, Asn or Lys; R$_{18}$ is Val, Nle or Met; R$_{19}$ and R$_{24}$ are selected from the group consisting of leu, Ile, ala, Gly, Val, Nle, Phe, Asn and Gln; R$_{20}$ is Glu or D-Glu; R$_{21}$ is Met, Nva, Ile, ala, leu, Nle, Val, Phe, Asn or Gln; $R_{22}$ is ala, Thr, Asp or Glu; $R_{23}$ is Arg, Orn, Har or Lys; $R_{25}$ is Asp or Glu; $R_{26}$ is Gln, Asn or Lys; $R_{27}$ is leu, Ile, ala, Val, Nva, Met, Nle, Phe, Asp, Asn, Gln or Glu; $R_{28}$ is ala, Arg or Lys; $R_{29}$ is Gln or Glu, $R_{32}$ is His, Gly, Tyr or ala; $R_{33}$ is Ser, Asn, leu, Thr or ala; $R_{36}$ is Lys, Orn, Arg, Har or leu; $R_{37}$ is leu or Tyr; $R_{39}$ is Glu or Asp; $R_{40}$ is Ile, Thr, Glu, ala, Val, leu, Nle, Phe, Nva, Gly or Gln; and $R_{41}$ is ala, Ile, Gly, Val, leu, Nle, Phe, Nva or Gln; or a nontoxic addition salt thereof. Antagonists in accordance with this formula exhibit excellent binding to pituitary receptors for native CRF. A preferred group of antagonists are those having the formula: Y-$R_{12}$-$R_{13}$-leu-leu-Arg-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-Gln-Ala-$R_{32}$-$R_{33}$-Asn-Arg-$R_{36}$-$R_{37}$-Nle-$R_{39}$-$R_{40}$-$R_{41}$-$NH_2$ wherein Y is Ac or hydrogen; $R_{12}$ is D-Phe, D-Tyr, D-Leu, D-His, D-Nal, D-Pal, D-Nle, D-Ile, D-Val, D-Met or Phe; $R_{13}$ is His, Tyr or Glu; $R_{17}$ is Glu, Asn or Lys; $R_{18}$ is Val, Nle or Met; $R_{19}$ and $R_{24}$ are selected from the group consisting of leu, Ile, ala, Gly, Val, Nle, Phe and Gln; $R_{20}$ is Glu or D-Glu; $R_{21}$ is Met, Nva, Ile, ala, leu, Nle, Val, Phe or Gln; $R_{22}$ is ala, Thr, Asp or Glu; $R_{23}$ is Arg, Orn, Har or Lys; $R_{25}$ is Asp or Glu; $R_{26}$ is Gln, Asn or Lys; $R_{27}$ is leu, Ile, ala, Val, Nva, Met, Nle, Phe, Asp, Asn, Gln or Glu; $R_{28}$ is ala, Arg or Lys; $R_{29}$ is Gln or Glu, $R_{32}$ is His, Gly, Tyr or ala; $R_{33}$ is Ser, Asn, leu, Thr or ala; $R_{36}$ is Lys, Orn, Arg, Har or leu; $R_{37}$ is leu or Tyr; $R_{39}$ is Glu or Asp; $R_{40}$ is Ile, Thr, Glu, ala, Val, leu, Nle, Phe, Nva, Gly or Gln; and $R_{41}$ is ala, Ile, Gly, Val, leu, Nle, Phe, Nva or Gln; or a nontoxic addition salt thereof. One analog of this group which has been found to be particularly long-acting is: [D-Phe$^{12}$, Nle$^{21,38}$, CML$^{37}$]-rCRF(12-41). A particularly preferred subgroup of this group of antagonists includes the following: $R_{12}$ is D-Phe, Phe or D-2Nal, $R_{13}$ is His, $R_{17}$ is Glu, $R_{18}$ a is Val, $R_{19}$ and $R_{37}$ are Leu, $R_{20}$ is Glu or D-Glu, $R_{21}$ is Nle, $R_{22}$ is Ala, $R_{23}$ is Arg, $R_{24}$ and $R_{28}$ are Ala, $R_{25}$ and $R_{39}$ are Glu, $R_{26}$ is Gln, $R_{27}$ is Leu, $R_{29}$ is Gln, $R_{32}$ is His, $R_{33}$ is Ser, $R_{36}$ is Arg, Lys, Har or Leu, $R_{40}$ is Ile and $R_{41}$ is Ala or Ile. One analog which has been found to be particularly potent is: [D-Phe$^{12}$, Nle$^{21,38}$]-rCRF(12-41).

The peptides are synthesized by a suitable method, such as by exclusively solid-phase techniques, by partial solid-phase techniques, by fragment condensation or by classical solution addition. Certain CRF antagonist sections which do not include D-isomer residues or unnatural amino acid residues may also be synthesized by recently developed recombinant DNA techniques.

Synthesis by the use of recombinant DNA techniques, for purposes of this application, should be understood to include the suitable employment of a structural gene coding for the desired form of CRF analog. Thus certain synthetic CRF peptides may be obtained by transforming a microorganism using an expression vector including a promoter and operator together with such structural gene and causing such transformed microorganism to express the CRF peptide. A non-human animal may also be used to produce certain CRF peptides by gene-farming using such a structural gene and the microinjection of embryos as described in WO83/01783 published 26 May 1983 and WO82/04443 published Dec. 23, 1982. Such synthetic CRF peptides are then suitably recovered from the animal by extraction from sera or the like.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

Also considered to be within the scope of the present invention are intermediates of the Formula (II): $X^1$-$R_{12}(X)$-$R_{13}(X$ or $X^5)$-leu-leu-Arg($X^3$)-$R_{17}(X^4, X^5$ or $X^6)$-$R_{18}$-$R_{19}(X^4)$-$R_{20}(X^5)$-$R_{21}$-$R_{22}(X^2$ or $X^5)$-$R_{23}(X^3$ or $X^6)$-$R_{24}(X^4)$-$R_{25}(X^5)$-$R_{26}(X^4$ or $X^6)$-$R_{27}(X^4$ or $X^5)$-$R_{28}(X^3$ or $X^6)$-$R_{29}(X^4$ or $X^5)$-Gln($X^4$)-ala-$R_{32}(X)$-$R_{33}(X^2$ or $X^4)$-Asn($X^4$)-Arg ($X^3$)-$R_{36}(X^3$ or $X^6)$-$R_{37}(X)$-Nle-$R_{39}(X^5)$-$R_{40}(X^2$ or $X^4$ or $X^5)$-$R_{41}(X^4)$-$X^7$ wherein: the R-groups are as hereinbefore defined.

$X^1$ is either hydrogen or an alpha-am protecting group. The alpha-amino protecting groups contemplated by $X^1$ are those known to be useful in the art in the step-wise synthesis of polypeptides. Among the classes of alpha-amino protecting groups covered by $X^1$ are (1) acyl-type protecting groups, such as formyl, acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenyl methyloxycarbonyl (FMOC), cyclopentyloxy-carbonyl, adamantyloxycarbonyl, and cyclohexyloxy-carbonyl; and (5) thiourethan-type protecting groups, such as phenylthiocarbonyl. The preferred alpha-amino protecting group is BOC.

$X^2$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the guanidino group of Arg or Har preferably selected from the class consisting of nitro, p-toluenesulfonyl(Tos), Z, adamantyloxycarbonyl and BOC, or is hydrogen. Tos is most preferred.

$X^4$ is hydrogen or a protecting group, preferably xanthyl(Xan), for the amido group of Asn or Gln.

$X^5$ is hydrogen or an ester-forming protecting group for the β- or y-carboxyl group of Asp or Glu, preferably selected from the class consisting of benzyl, 2,6-dichlorobenzyl, methyl, ethyl and t-butyl ester. OBzl is most preferred.

$X^6$ is hydrogen or a protecting group for the side chain amino substituent of Lys or Orn. Illustrative of suitable side chain amino protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore.

When His is present, X is hydrogen or a protecting group for the imidazole nitrogen such as Tos or 2,4-dinitrophenyl(DNP), and when Tyr is present, X is hydrogen or a protecting group for the hydroxyl group such as DCB. When Met is present, the sulfur may be protected, if desired, with oxygen.

The selection of a side chain amino protecting group is not critical except that it should must be one which is not removed during deprotection of the alpha-amino groups during the synthesis. Hence, the alpha-amino protecting group and the side chain amino protecting group cannot be the same.

$X^7$ is $NH_2$, a protecting group such as an ester or an anchoring bond used in solid phase synthesis for linking to a solid resin support, preferably one represented by the formula: -NH-benzhydrylamine (BHA) resin support and -NH-paramethylbenzhydrylamine (MBHA) resin support. Cleavage from a BHA or MBHA resin directly gives the CRF analog amide. By employing a methyl-derivative of such a resin, a methyl-substituted amide can be created, which is considered to be the equivalent thereof.

In the formula for the intermediate, at least one of X, $X^1$, $X^2$, $X^3$, $X^4$, $X^5$ and $X^6$ is a protecting group. The particular amino acid chosen for each R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

For the acyl group at the N-terminal represented by Y, acetyl, formyl, acrylyl and benzoyl are preferred.

Thus, the present invention is also considered to provide a process for the manufacture of compounds defined by the Formula (I) comprising (a) forming a peptide having at least one protective group and having the Formula (II) wherein: X, $X^1$, $X^2$, $X^3$, $X^4$, $X^5$ and $X^6$ are each either hydrogen or a protective group, and $X^7$ is either a protective group or an anchoring bond to resin support or $NH_2$ and (b) splitting off the protective group or groups or anchoring bond from said peptide of the Formula (II) and (c) if desired, converting a resulting peptide into a nontoxic addition salt thereof.

When the peptides are prepared by chemical synthesis, they are preferably prepared using solid phase synthesis, such as that described by Merrifield, J. Am. Chem. Soc., 85, p 2149 (1964), although other equivalent chemical syntheses known in the art can also be used as previously mentioned. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for an antagonist based upon human CRF can be prepared by attaching alpha-amino-protected Ile to a BHA resin.

Ile protected by BOC is coupled to the BHA resin using methylene chloride and dimethylformamide (DMF). Following the coupling of BOC-Ile to the resin support, the alpha-amino protecting group is removed, as by using trifluoroacetic acid(TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0° C. and room temperature. Other standard cleaving reagents and conditions for removal of specific alpha-amino protecting groups may be used as described in Schroder & Lubke, "The Peptides", 1 pp 72–75 (Academic Press 1965).

After removal of the alpha-amino protecting group of Ile, the remaining alpha-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide(DCC) and N,N'-diisopropyl carbodiimide(DICI).

The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl) carbodiimide. Other activating reagents and their use in peptide coupling are described by Schroder & Lubke, supra, in Chapter III and by Kapoor, J. Phar. Sci., 59, pp 1–27 (1970).

Each protected amino acid or amino acid sequence is introduced into the solid phase reactor in about a four-fold excess, and the coupling is carried out in a medium of dimethylformamide (DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., Anal. Biochem. 34, 595 (1970). In cases where incomplete coupling occurs, the coupling procedure is repeated before removal of the alpha-amino protecting group prior to the coupling of the next amino acid. The coupling reactions can be performed automatically, as on a Beckman 990 automatic synthesizer, using a program such as that reported in Rivier et al., Biopolymers, 1978, 17, pp.1927–1938.

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$ and $X^6$ and the alpha-amino protecting group $X^1$ (unless it is an acyl group which is intended to be present in the final peptide), to obtain the peptide. When using hydrogen fluoride for cleaving, anisole or cresole and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate S-alkylation.

The following Example sets forth the preferred method for synthesizing CRF antagonists by the solid-phase technique.

EXAMPLE I

The synthesis of the [D-Phe$^{12}$, Nle$^{21,38}$]-human CRF(12-41) having the formula: H-D-Phe-His-Leu-Leu-Arg-Glu-Val-Leu-Glu-Nle-Ala-A rg-Ala-Glu-Gln-Leu-Ala-Gln-Gln-Ala-His-Ser-Asn-A rg-Lys-Leu-Nle-Glu-Ile-Ile-NH$_2$ is conducted in a stepwise manner on a MBHA hydrochloride resin, such as available from Bachem, Inc., having a substitution range of about 0.1 to 0.7 mmoles/gm. resin. The synthesis is performed on an automatic Beckman 990B peptide synthesizer using a suitable program, preferably as follows:

| STEP MIN. | REAGENTS AND OPERATIONS | MIX TIMES |
|---|---|---|
| 1 | CH$_2$Cl$_2$ wash-80 ml. (2 times) | 3 |
| 2 | Methanol(MeOH) wash-30 ml. (2 times) | 3 |
| 3 | CH$_2$Cl$_2$ wash-80 ml. (3 times) | 3 |
| 4 | 50 percent TFA plus 5 percent 1,2-ethane-dithiol in CH$_2$Cl$_2$-70 ml. (2 times) | 12 |
| 5 | Isopropanol wash-80 ml. (2 times) | 3 |
| 6 | TEA 12.5 percent in CH$_2$Cl$_2$-70 ml. (2 times) | 5 |
| 7 | MeOH wash-40 ml. (2 times) | 2 |
| 8 | CH$_2$Cl$_2$ wash-80 ml. (3 times) | 3 |
| 9 | Boc-amino acid (10 mmoles) in 30 ml. of either DMF or CH$_2$Cl$_2$, depending upon the solubility of the particular protected amino acid, (1 time) plus DCC (10 mmoles) in CH$_2$Cl$_2$ | 30-300 |

Coupling of BOC-Ile results in the substitution of about 0.35 mmol. Ile per gram of resin. All solvents that are used are carefully degassed, preferably by sparging with an inert gas, e.g. helium or nitrogen.

After deprotection and neutralization, the peptide chain is built step-by-step on the resin. Generally, one to two mmol. of BOC-protected amino acid in methylene chloride is used per gram of resin, plus one equivalent of 2 molar DCC in methylene chloride, for two hours. When BOC-Arg(Tos) is being coupled, a mixture of 50% DMF and methylene chloride is used. Bzl is used as the hydroxyl side-chain protecting group for Ser. P-nitrophenyl ester(ONp) can be used to activate the carboxyl end of Asn or Gln, and for example, BOC-Asn(ONp) can be coupled overnight using one equivalent of HOBt in a 50% mixture of DMF and methylene chloride. The amido group of Asn or Gln is protected by Xan when DCC coupling is used instead of the active ester method. 2-Cl-Z is used as the protecting group for the Lys side chain. Tos is used to protect the guanidino group of Arg and the imidazole group of His, and the side chain carboxyl group of Glu is protected by OBzl. At the end of the synthesis, the following composition is obtained BOC-D-Phe-His(Tos)-Leu-Leu-Arg(Tos)-G lu(OBzl)-Val-Leu-Glu(OBzl)-Nle-Ala-Arg(Tos)-Ala-G lu(OBzl)-Gln(Xan)-Leu-Ala-Gln(Xan)-Gln(Xan)-Ala-H is(Tos)-Ser(Bzl)-Asn(Xan)-Arg(Tos)-Lys(2-Cl-Z)-Leu-N le-Glu(OBzl)-Ile-Ile-MBHA resin support. Xan may have been partially or totally removed by TFA treatment used to deblock the alpha-amino protecting group.

In order to cleave and deprotect the resulting protected peptide-resin, it is treated with 1.5 ml. anisole, 0.5 ml. of methylethylsulfide and 15 ml. hydrogen fluoride (HF) per gram of peptide-resin, first at $-20°$ C. for 20 min. and then at 0° C. for one-half hour. After elimination of the HF under high vacuum, the resin-peptide is washed alternately with dry diethyl ether and chloroform, and the peptides are then extracted with degassed 2N aqueous acetic acid and separated from the resin by filtration.

The peptide is purified by gel permeation followed by semi-preparative HPLC as described in Rivier et al., *Peptides: Structure and Biological Function* (1979) pp. 125-128, and River et al. *J. Chromatography* (1983). The chromatographic fractions are carefully monitored by HPLC, and only the fractions showing substantial purity are pooled.

Specific optical rotation of the hCRF peptide, which is synthesized and purified in the foregoing manner, is measured on a Perkin Elmer Model 241 Polarimeter as $[\alpha]_D^{22} = -39.4 \pm 1.0$ (c=0.5 in 50% acetic acid) (with correction for the presence of H$_2$O and TFA); it has a purity of about 95%. To check whether the precise sequence is achieved, the CRF peptide is hydrolyzed in sealed evacuated tubes containing constant boiling HCl, 3 μl of thioglycol/ml. and 1 nmol of Nle (as an internal standard) for 9 hours at 140° C. Amino acid analysis of the hydrolysate using a Beckman 121 MB amino acid analyzer shows the following amino acid ratios: Asx(0.9), Glx(7.1), Ala(3.9), Nle(1.9), Val(1.1), Ser(1.1), Ile(2.1), Leu(5.0), Phe(0.9), Lys(1.0), His(2.1) and Arg(3.0), which confirms that the 30-residue peptide structure has been obtained.

EXAMPLE II

The synthetic peptide [D-Phe$^{12}$, Nle$^{21,38}$, Arg$^{36}$]-hCRF(12-41) having the formula: H-D-Phe-His-L eu-Leu-Arg-Glu-Val-Leu-Glu-Nle-Ala-Arg-Ala-Glu-Gln-L eu-Ala-Gln-Gln-Ala-His-Ser-Asn-Arg-Arg-Leu-Nle-Glu-I le-Ile-NH$_2$ is synthesized generally in accordance with the procedure set forth in Example I.

Specific optical rotation of the hCRF peptide, which is synthesized and purified in the foregoing manner, is measured on a Perkin Elmer Model 241 Polarimeter as $[\alpha]_D^{22} = -27.7 \pm 1.0$ (c=0.5 in 50% acetic acid) (with correction for the presence of H$_2$O and TFA); it has a purity of about 99%.

The peptide is judged to be homogeneous using thin layer chromatography and several different solvent systems. It is specifically subjected to isocratic reversed-phase high pressure liquid chromatography using the Waters HPLC system described above with a 0.46×25 cm column packed with 5μm C$_{18}$ silica, 300 Å pore size. The buffer used is an aqueous 0.1% trifluoroacetic acid solution consisting of 1 0 ml. of TFA per 1000 ml. of solution plus 42.6% acetonitrile. The determination is run at room temperature. The flow rate is 2.0 ml. per minute, and the retention volume is 10.4 ml.

Amino acid analysis of the resultant, purified peptide is consistent with the formula for the prepared peptide and confirms that the 30-residue peptide structure is obtained.

EXAMPLE III

The synthetic peptide [D-Phe$^{12}$, Nle$^{21,38}$, CML$^{37}$]-hCRF(12-14) having the formula: H-D-Phe-His-L eu-Leu-Arg-Glu-Val-Leu-Glu-Nle-Ala-Arg-Ala-Glu-Gln-L eu-Ala-Gln-Gln-Ala-His-Ser-Asn-Arg-Lys-CML-Nle-Glu-Il e-Ile-NH$_2$ is synthesized generally in accordance with the procedure set forth in Example I.

Specific optical rotation of the hCRF peptide, which is synthesized and purified in the foregoing manner, is measured on a Perkin Elmer Model 241 Polarimeter as $[\alpha]_D^{22} = -57° \pm 1.0°$ (c=1.0 in 1% acetic acid) (with correction for the presence of H₂O and TFA); it has a purity of about 99%.

The peptide is judged to be homogeneous using thin layer chromatography and several different solvent systems. It is specifically subjected to isocratic reversed-phase high pressure liquid chromatography using the Waters HPLC system described above with a 0.46×25 cm column packed with 5μm C$_{18}$ silica, 300 Å pore size. The buffer used is an aqueous 0.1% trifluoroacetic acid solution consisting of 1.0 ml. of TFA per 1000 ml. of solution plus 35.4% acetonitrile. The determination is run at room temperature. The flow rate is 2.0 ml. per minute, and the retention volume is 11.8 ml.

Amino acid analysis of the resultant, purified peptide is consistent with the formula for the prepared peptide and confirms that the 30-residue peptide structure is obtained.

The synthetic CRF antagonists from Examples I, II, and III are examined for their effects on the secretion of ACTH and β-endorphin in vitro. The effectiveness of synthetic CRF antagonists to block the secretion of ACTH and β-endorphin by cultured rat pituitary cells is measured using the procedure as generally set forth in Vale et al., *Endocrinology*. 91, 562 (1972).

The antagonist Peptide No. I, prepared in Example I, is tested using the procedure set forth in detail in J. River et al., *Science*, 224, 889–891 (1984) to determine its effect in blocking by 50% the secretion of ACTH stimulated by a 1 nM dose of oCRF. Compared to AHC(9-41), a potent CRF antagonist disclosed in U.S. Pat. No. 4,605,642, this peptide was more than 17 times as potent. The specificity of this inhibition is demonstrated by the finding of no effect of the standard antagonist on GRF-stimulated secretion of GH, GnRH-stimulated secretion of LH and FSH or TRF-stimulated secretion of TSH and prolactin. The effects of the antagonist on a number of different concentrations of oCRF and the ability of several different concentrations of Peptide No. I to inhibit ACTH secretion stimulated by a constant dose of oCRF (1 nM) are considered to demonstrate competitive inhibition. Similar testing shows that Peptide No. II, prepared in Example II, is more than 15 times as potent as AHC(9-41), and that Peptide No. III measures about 0.511 (0.141–1.620) relative to Peptide No. I.

The in vivo effect of CRF antagonists Nos. I and II is tested on the spontaneous ACTH release by adrenalectomized rats. The iv injection of 3 mg/kg BW (about 2.7 nmole) causes a marked decrease in plasma ACTH levels (measured as described in Vale et al. *Science*, 213,1394, 1981), which is statistically significant for 2 hours. In the intact, non-anesthetized rats, the antagonists induce a dose-related inhibition of CRF-induced ACTH secretion, which is significant at the 0.09 μmole dose level, and prevent most, but not all, of the ACTH rise due to ether-exposure.

These results indicate that administration of CRF antagonists reduces the spontaneous ACTH release observed after removal of the corticosteroid feedback, totally blocks the ACTH secretion caused by CRF, and inhibits most of the stressor-induced ACTH release in intact rats. Such data are comparable to those previously obtained with an antiserum to CRF which demonstrate the role played by endogenous CRF in regulating ACTH secretion, Rivier, C. et al., *Science*, 218, 377-9 (1982).

Synthetic hCRF has been shown to be a powerful stimulator of secretion of ACTH and β-endorphin-like (β-END-LI) immunoactivities in vivo in several rat preparations. Plasma levels of ACTH and β-END-LI are elevated for at least 5–20 minutes following the intraveneous administration of hCRF to nembutal-anesthesized male rats and to quiescent male or female rats with indwelling intravenous cannulae. In addition, hCRF is found to have a dramatic effect to lower blood pressure in rats and dogs. These antagonists should counteract such effects.

Peptide No. III is then similarly tested in vivo against the Standard using iv injection. At a dose of 0.1 mg., Peptide No. III shows effectiveness in lowering ACTH release for about 40 minutes whereas the Standard shows no measurable effect at this level. In two runs at dosages of 0.5 mg., the Standard demonstrated bioactivity for about 40 minutes each time whereas Peptide No. III demonstrated bioactivity for periods of about 60 minutes and about 90 minutes, respectively.

EXAMPLE IV

The peptide [Nle$^{21,38}$]-hCRF(12-41) having the formula: H-Phe-His-Leu-Leu-Arg-Glu-Val-Leu-Glu-Nle-Ala-Arg-Ala-G lu-Gln-Leu-Ala-Gln-Gln-Ala-His-Ser-Asn-Arg-Lys-Leu-N le-Glu-Ile-Ile-NH₂ is synthesized.

Specific optical rotation of the hCRF peptide, which is synthesized and purified in the foregoing manner, is measured on a Perkin Elmer Model 241 as $[\alpha]_D^{22} = -27.2 \pm 1.0$ (c=0.5 in 50% acetic acid) (with correction for the presence of H₂O and TFA), and it has a purity of about 99%.

The peptide is judged to be homogeneous using thin layer chromatography and several different solvent systems. It is specifically subjected to isocratic reversed-phase high pressure liquid chromatography using the Waters HPLC system described above with a 0.46×25 cm column packed with 5 μm C$_{18}$ silica, 300 Å pore size. The buffer used is an aqueous 0.1% trifluoroacetic acid solution consisting of 1.0 ml. of TFA per 1000 ml. of solution plus 36.0% acetonitrile. The determination is run at room temperature. The flow rate is 2.0 ml. per minute, and the retention volume is 9.5 ml.

Amino acid analysis of the resultant, purified peptide is consistent with the formula for the prepared peptide and confirms that the β-residue peptide structure had been obtained.

Testing in accordance with the general procedure set forth hereinbefore shows that it likewise inhibits the secretion of ACTH and β-END-LI. The peptide is more than 12 times as potent as AHC(9-41).

EXAMPLE V

The peptide [Nle$^{21,38}$]-hCRF(9-41) having the formula: H-Asp-Leu-Thr-Phe-His-Leu-Leu-Arg-Glu-Val-Leu-Glu-Nle-A la-Arg-Ala-Glu-Gln-Leu-Ala-Gln-Gln-Ala-His-Ser-Asn-A rg-Lys-Leu-Nle-Glu-Ile-Ile-NH₂ is synthesized.

Specific optical rotation of the hCRF peptide, which is synthesized and purified in the foregoing manner, is measured on a Perkin Elmer Model 241 as $[\alpha]_D^{22} = -17.6 \pm 1.0$ (c=0.5 in 50% acetic acid) (with correction for the presence of H₂O and TFA), and it has a purity of about 99%.

The peptide is judged to be homogeneous using thin layer chromatography and several different solvent systems. It is specifically subjected to isocratic reversed-phase high pressure liquid chromatography using the Waters HPLC system described above with a 0.46×25 cm column packed with 5 μm C$_{18}$ silica, 300 Å pore size. The buffer used is an aqueous 0.1% trifluoroacetic acid solution consisting of 1.0 ml. of TFA per 1000 ml. of solution plus 39.6% acetonitrile. The determination is run at room temperature. The flow rate is 2.0 ml. per minute, and the retention volume is 10.1 ml.

Amino acid analysis of the resultant, purified peptide is consistent with the formula for the prepared peptide and confirms that the 33-residue peptide structure has been obtained.

Testing in accordance with the general procedure set forth in Example III shows that it likewise inhibits the secretion of ACTH and β-END-LI. The peptide is more than 6 times as potent as AHC(9-41).

EXAMPLE VI

The peptide [Nle$^{38}$]-Carp Urotensin I(12-41) having the formula: H-Phe-His-Leu-Leu-Arg-Asn-Met-Ile-Glu-Met-Ala-Arg-Asn-G lu-Asn-Gln-Arg-Glu-Gln-Ala-Gly-Leu-Asn-Arg-Lys-Tyr-N le-Asp-Glu-Val-NH$_2$ is synthesized. Testing in accordance with the general procedure set forth hereinbefore shows that it likewise inhibits the secretion of ACTH and β-END-LI.

EXAMPLE VII

The peptide [Nle$^{21,38}$, Arg$^{36}$]-hCRF (9-41) having the formula: H-Asp-Leu-Thr-Phe-His-Leu-Leu-Arg-Glu-Val-Leu-Glu-Nle-A la-Arg-Ala-Glu-Gln-Leu-Ala-Gln-Gln-Ala-His-Ser-Asn-A rg-Arg-Leu-Nle-Glu-Ile-Ile-NH$_2$ is synthesized.

Specific optical rotation of the hCRF peptide, which is synthesized and purified in the foregoing manner, is measured on a Perkin Elmer Model 241 as $[\alpha]_D^{22} = -16.0 \pm 1.0$ (c=0.5 in 50% acetic acid) (with correction for the presence of H$_2$O and TFA); it has a purity of about 99%.

The peptide is judged to be homogeneous using thin layer chromatography and several different solvent systems. It is specifically subjected to isocratic reversed-phase high pressure liquid chromatography using the Waters HPLC system described above with a 0.46×25 cm column packed with 5 μm C$_{18}$ silica, 300 Å pore size. The buffer used is an aqueous 0.1% trifluoroacetic acid solution consisting of 1.0 ml. of TFA per 1000 ml. of solution plus 39.0% acetonitrile. The determination is run at room temperature. The flow rate is 2.0 ml. per minute, and the retention volume is 9.1 ml.

Amino acid analysis of the resultant, purified peptide is consistent with the formula for the prepared peptide and confirms that the 33-residue peptide structure has been obtained.

Testing in accordance with the general procedure set forth in hereinbefore shows that it likewise inhibits the secretion of ACTH and β-END-LI. The peptide is about twice as potent as AHC(9-41).

EXAMPLE VIII

The peptide [Nle$^{18,21,38}$]-Carp Urotensin I(12-41) having the formula: H-Phe-His-Leu-Leu-Arg-A sn-Nle-Ile-Glu-Nle-Ala-Arg-Asn-Glu-Asn-Gln-Arg-Glu-G ln-Ala-Gly-Leu-Asn-Arg-Lys-Tyr-Nle-Asp-Glu-Val-NH$_2$ is synthesized. Testing in accordance with the general procedure set forth hereinbefore shows that it likewise inhibits the secretion of ACTH and β-END-LI.

EXAMPLE IX

The peptide [Nle$^{21,38}$, Arg$^{37}$]-hCRF(12-41) having the formula: H-Phe-His-Leu-Leu-Arg-Glu-Val-Leu-Glu-Nle-Ala-Arg-Ala-G lu-Gln-Leu-Ala-Gln-Gln-Ala-His-Ser-Asn-Arg-Arg-Leu-N le-Glu-Ile-Ile-NH$_2$ is synthesized.

Specific optical rotation of the hCRF peptide, which is synthesized and purified in the foregoing manner, is measured on a Perkin Elmer Model 241 as $[\alpha]_D^{22} = -23.7 \pm 1.0$ (c=0.5 in 50% acetic acid) (with correction for the presence of H$_2$O and TFA), and it has a purity of about 98%.

The peptide is judged to be homogeneous using thin layer chromatography and several different solvent systems. It is specifically subjected to isocratic reversed-phase high pressure liquid chromatography using the Waters HPLC system described above with a 0.46×25 cm column packed with 5 μm C$_{18}$ silica, 300 Å pore size. The buffer used is an aqueous 0.1% trifluoroacetic acid solution consisting of 1.0 ml. of TFA per 1000 ml. of solution plus 36.6% acetonitrile. The determination is run at room temperature. The flow rate is 2.0 ml. per minute, and the retention volume is 10.1 ml.

Amino acid analysis of the resultant, purified peptide is consistent with the formula for the prepared peptide and confirms that the 30-residue peptide structure has been obtained.

Testing in accordance with the general procedure set forth hereinbefore shows that it likewise inhibits the secretion of ACTH and β-END-LI. The peptide is more than 6 times as potent as AHC(9-41).

EXAMPLE X

The peptide [D-2Nal$^{12}$, Nle$^{21,38}$]-hCRF(12-41) having the formula: H-D-2Nal-His-Leu-Leu-Arg-Glu-Val-Leu-Glu-Nle-Ala-Arg-A la-Glu-Gln-Leu-Ala-Gln-Gln-Ala-His-Leu-Asn-Arg-Lys-Leu -Nle-Glu-Ile-Ile-NH$_2$ is synthesized.

Specific optical rotation of the hCRF peptide, which is synthesized and purified in the foregoing manner, is measured on a Perkin Elmer Model 241 as $[\alpha]_D^{22} = -26.8 \pm 1.0$ (c=0.5 in 50% acetic acid) (with correction for the presence of H$_2$O and TFA), and has a purity of about 60%.

The peptide is judged to be homogeneous using thin layer chromatography and several different solvent systems. It is specifically subjected to isocratic reversed-phase high pressure liquid chromatography using the Waters HPLC system described above with a 0.46×25 cm column packed with 5 μm C$_{18}$ silica, 300 Å pore size. The buffer used is an aqueous 0.1% trifluoroacetic acid solution consisting of 1.0 ml. of TFA per 1000 ml. of solution plus 39% acetonitrile. The determination is run at room temperature. The flow rate is 2.0 ml. per minute, and the retention volume is 8.9 ml.

Amino acid analysis of the resultant, purified peptide is consistent with the formula for the prepared peptide and confirmed that the 30-residue peptide structure had been obtained.

Testing in accordance with the general procedure set forth hereinbefore shows that it likewise inhibits the secretion of ACTH and β-END-LI. The peptide is about 9 times as potent as AHC(9-41).

EXAMPLE XI

The peptide [D-Phe$^{12}$, Nle$^{21,38}$, Arg$^{36}$, CML$^{37}$]oCRF(12-41) having the formula: H-D-Phe-His-Leu-Leu-Arg-Glu-Val-Leu-Glu-Nle-Thr-Lys-A la-Asp-Gln-Leu-Ala-Gln-Gln-Ala-His-Ser-Asn-Arg-Arg-C ML-Nle-Asp-Ile-Ala-NH$_2$ is synthesized. Testing in accordance with the general procedure set forth hereinbefore shows that it likewise inhibits the secretion of ACTH and β-END-LI.

EXAMPLE XII

The peptide [D-Phe$^{12}$, Nle$^{21,38}$, Leu$^{36}$]-hCRF (12-41) having the formula: H-D-Phe-His-Leu-Leu-A rg-Glu-Val-Leu-Glu-Nle-Ala-Arg-Ala-Glu-Gln-Leu-Ala-G ln-Gln-Ala-His-Ser-Asn-Arg-Leu-Leu-Nle-Glu-Ile-Ile-NH$_2$ is synthesized.

Specific optical rotation of the hCRF peptide, which is synthesized and purified in the foregoing manner, is measured on a Perkin Elmer Model 241 as $[\alpha]_D^{22} = -22.7 \pm 1.0$ (c=0.5 in 50% acetic acid) (with correction for the presence of H$_2$O and TFA), and it has a purity of about 68.2%.

The peptide is judged to be homogeneous using thin layer chromatography and several different solvent systems. It is specifically subjected to isocratic reversed-phase high pressure liquid chromatography using the Waters HPLC system described above with a 0.46×25 cm column packed with 5 μm C$_{18}$ silica, 300 Å pore size. The buffer used is an aqueous 0.1% trifluoroacetic acid solution consisting of 1.0 ml. of TFA per 1000 ml. of solution plus 45.0% acetonitrile. The determination is run at room temperature. The flow rate is 2.0 ml. per minute, and the retention volume is 9.0 ml.

Amino acid analysis of the resultant, purified peptide is consistent with the formula for the prepared peptide and confirms that the 30-residue peptide structure had been obtained.

Testing in accordance with the general procedure set forth hereinbefore shows that it likewise inhibits the secretion of ACTH and β-END-LI. The peptide is about 3 times as potent as AHC(9-41).

EXAMPLE XIII

The peptide [Acetyl-Asp$^9$, Gly$^{19}$, Nle$^{38}$, Asp$^{39}$, Nva$^{40}$]-hCRF(9-41) having the formula: Ac-Asp-Leu-Thr-P he-His-Leu-Leu-Arg-Glu-Val-Gly-Glu-Met-Ala-Arg-Ala-G lu-Gln-Leu-Ala-Gln-Gln-Ala-His-Ser-Asn-Arg-Lys-Leu-N Nle-Asp-Nva-Ile-NH$_2$ is synthesized. Testing in accordance with the general procedure set forth hereinbefore shows that it likewise inhibits the secretion of ACTH and β-END-LI.

EXAMPLE XIV

The peptide [Gln$^{19}$, Lys$^{23}$, Val$^{24}$, CMA$^{33}$, Nle$^{38}$]-hCRF(12-41) having the formula: H-Phe-His-Leu-L eu-Arg-Glu-Val-Gln-Glu-Met-Ala-Lys-Val-Glu-Gln-Leu-A la-Gln-Gln-Ala-His-CMA-Asn-Arg-Lys-Leu-Nle-Glu-Ile-I le-NH$_2$ is synthesized. Testing in accordance with the general procedure set forth hereinbefore shows that it likewise inhibits the secretion of ACTH and β-END-LI.

EXAMPLE XV

The peptide [Nle$^{21,38}$, Gly$^{24}$, Tyr$^{32}$, Orn$^{36}$]-hCRF (10-41) having the formula: H-Leu-Thr-Phe-His-Leu-L eu-Arg-Glu-Val-Leu-Glu-Nle-Ala-Arg-Gly-Glu-Gln-Leu-A la-Gln-Gln-Ala-Tyr-Ser-Asn-Arg-Orn-Leu-Nle-Glu-Ile-I le-NH$_2$ is synthesized. Testing in accordance with the general procedure set forth hereinbefore shows that it likewise inhibits the secretion of ACTH and β-END-LI.

EXAMPLE XVI

The peptide [Ala$^{21}$, Nle$^{37}$, Gln$^{40}$]-sauvagine (10-40) having the formula: H-Ser-Leu-Glu-Leu -Leu-Arg-Lys-Met-Ile-Glu-Ile-Ala-Lys-Gln-Glu-Lys-Glu-L ys-Gln-Gln-Ala-Ala-Asn-Asn-Arg-Leu-Leu-Nle-Asp-Thr-G ln-NH$_2$ is synthesized. Testing in accordance with the general procedure set forth hereinbefore shows that it likewise inhibits the secretion of ACTH and β-END-LI.

EXAMPLE XVII

The peptide [Ala$^{20}$, Har$^{22}$, Nle$^{37}$, Phe$^{39}$]-sauvagine (11-40) having the formula: H-Leu-Glu-Leu-Leu-Arg-Lys-Met-Ile-Glu-Ala-Glu-Har-Gln-G lu-Lys-Glu-Lys-Gln-Gln-Ala-Ala-Asn-Asn-Arg-Leu-Leu-N le-Asp-Phe-Ile-NH$_2$ is synthesized. Testing in accordance with the general procedure set forth hereinbefore shows that it likewise inhibits the secretion of ACTH and β-END-LI.

EXAMPLE XVIII

The peptide [Val$^{18,20}$, Ile$^{26}$, Nle$^{37}$, Gly$^{40}$]-sauvagine(11-40) having the formula: H-Leu-Glu-L eu-Leu-Arg-Lys-Met-Val-Glu-Val-Glu-Lys-Gln-Glu-Lys-I le-Lys-Gln-Gln-Ala-Ala-Asn-Asn-Arg-Leu-Leu-Nle-Asp-T hr-Gly-NH$_2$ is synthesized. Testing in accordance with the general procedure set forth hereinbefore shows that it likewise inhibits the secretion of ACTH and β-END-LI.

EXAMPLE XIX

The peptide [4FD-Phe$^{12}$, CML$^{14,15,19,27,33,37}$, CMA$^{22,32,41}$, Nle$^{38}$]-AHC(12-41) having the formula: H-4FD-Phe-Glu-CML-CML-Arg-Glu-Met-CML-Glu-Met-CMA-Lys-A la-Glu-Gln-CML-Ala-Glu-Gln-Ala-CMA-CML-Asn-Arg-Leu-C ML-Nle-Glu-Glu-CMA-NH$_2$. Testing in accordance with the general procedure set forth hereinbefore shows that it likewise inhibits the secretion of ACTH and β-END-LI.

EXAMPLE XX

The peptide [4ClD-Phe$^{12}$, Nle$^{18,21,38}$]-AHC(9-41) having the formula: H-Asp-Leu-Thr-4ClD-Phe-His-Leu-Leu-Arg-Glu-Nle-Leu-Glu -Nle-Ala-Lys-Ala-Glu-Gln-Glu-Ala-Glu-Gln-Ala-Ala-Leu-A sn-Arg-Leu-Leu-Nle-Glu-Glu-Ala-NH$_2$ is synthesized. Testing in accordance with the general procedure set forth hereinbefore shows that it likewise inhibits the secretion of ACTH and β-END-LI.

EXAMPLE XXI

The peptide [D-Phe$^{12}$, Met$^{27}$, Nle$^{21,38}$]-AHC (12-41) having the formula: H-D-Phe-His-Leu-Leu-Arg-Glu-Met-Leu-Glu-Nle-Ala-Lys-A la-Glu-Gln-Met-Ala-Glu-Gln-Ala-Ala-Leu-Asn-Arg-Leu-L eu-Nle-Glu-Glu-Ala-NH$_2$ is synthesized. Testing in accordance with the general procedure set forth hereinbefore shows that it likewise inhibits the secretion of ACTH and β-END-LI.

EXAMPLE XXII

The peptide [Nle$^{18,38}$, Leu$^{21}$, Ala$^{27}$]-AHC (12-41) having the formula: H-Phe-His-Leu-Leu-Arg-G lu-Nle-Leu-Glu-Leu-Ala-Lys-Ala-Glu-Gln-Ala-Ala-Glu-G ln-Ala-Ala-Leu-Asn-Arg-Leu-Leu-Nle-Glu-Glu-Ala-NH$_2$ is synthesized. Testing in accordance with the general procedure set forth hereinbefore shows that it likewise inhibits the secretion of ACTH and β-END-LI.

EXAMPLE XXIII

The peptide [Leu$^{12}$, Glu$^{13,22}$, Lys$^{26}$, Nle$^{38}$]-AHC(12-41) having the formula: H-Leu-Glu-Leu-Leu-Arg-G lu-Met-Leu-Glu-Met-Glu-Lys-Ala-Glu-Lys-Glu-Ala-Glu-G ln-Ala-Ala-Leu-Asn-Arg-Leu-Leu-Nle-Glu-Glu-Ala-NH$_2$. Testing in accordance with the general procedure set forth hereinbefore shows that it likewise inhibits the secretion of ACTH and $\beta$-END-LI.

EXAMPLE XXIV

The synthetic peptide [D-Ile$^{12}$, Tyr$^{13}$, CMA$^{28}$, Nle$^{38}$]-AHC(12-41) having the formula: H-D-Ile-Tyr-Leu-L eu-Arg-Glu-Met-Leu-Glu-Met-Ala-Lys-Ala-Glu-Gln-Glu-C MA-Glu-Gln-Ala-Ala-Leu-Asn-Arg-Leu-Leu-Nle-Glu-Glu-A la-NH$_2$ is synthesized. Testing in accordance with the general procedure set forth hereinbefore shows that it likewise inhibits the secretion of ACTH and $\beta$-END-LI.

EXAMPLE XXV

The peptide [D-Leu$^{12}$, Glu$^{13}$, Ala$^{33}$, Nle$^{38}$]-AHC(12-41) having the formula: H-D-Leu-Glu-Leu-Leu-A rg-Glu-Met-Leu-Glu-Met-Ala-Lys-Ala-Glu-Gln-Glu-Ala-G lu-Gln-Ala-Ala-Ala-Asn-Arg-Leu-Leu-Nle-Glu-Glu-Ala-NH$_2$. Testing in accordance with the general procedure set forth hereinbefore shows that it likewise inhibits the secretion of ACTH and $\beta$-END-LI.

EXAMPLE XXVI

The peptide [CML$^{14,19,27,36}$, Nle$^{38}$]-AHC(12-41) having the formula: H-Phe-His-CML-Leu-Arg-Glu-Met-CML-Glu-Met-Ala-Lys-Ala-G lu-Gln-CML-Ala-Glu-Gln-Ala-Ala-Leu-Asn-Arg-CML-Leu-N le-Leu-Glu-Glu-Ala-NH$_2$. Testing in accordance with the general procedure set forth hereinbefore shows that it likewise inhibits the secretion of ACTH and $\beta$-END-LI.

EXAMPLE XXVII

The peptide [D-Nle$^{12}$, Nle$^{18,21,38}$, Asn$^{19}$, Asp$^{22}$, Phe$^{27}$]-AHC(12-41) having the formula: H-D-Nle-His-Leu-Leu-Arg-Glu-Nle-Asn-Glu-Nle-Asp-Lys-A la-Glu-Gln-Phe-Ala-Glu-Gln-Ala-Ala-Leu-Asn-Arg-Leu-L eu-Nle-Glu-Glu-Ala-NH$_2$ is synthesized. Testing in accordance with the general procedure set forth hereinbefore shows that it likewise inhibits the secretion of ACTH and $\beta$-END-LI.

EXAMPLE XXVIII

The peptide [D-Val$^{12}$, Nle$^{21,38}$, Ile$^{24,27}$, Nva$^{41}$]-hCRF(11-41) having the formula: H-Thr-D-Val-His-L eu-Arg-Glu-Val-Leu-Glu-Nle-Ala-Arg-Ile-Glu-Gln-I le-Ala-Gln-Gln-Ala-His-Ser-Asn-Arg-Lys-Leu-Nle-Glu-I le-Nva-NH$_2$ is synthesized. Testing in accordance with the general procedure set forth hereinbefore shows that it likewise inhibits the secretion of ACTH and $\beta$-END-LI.

EXAMPLE XXIX

The peptide [Acrylyl-Leu$^{10}$, Val$^{27}$, Nle$^{38}$, Ala$^{40}$, Leu$^{41}$]-hCRF(10-41) having the formula: Acr-Leu-Thr-Phe-H is-Leu-Leu-Arg-Glu-Val-Leu-Glu-Met-Ala-Arg-Ala-Glu-G ln-Val-Ala-Gln-Gln-Ala-His-Ser-Asn-Arg-Lys-Leu-Nle-G lu-Ala-Leu-NH$_2$ is synthesized. Testing in accordance with the general procedure set forth hereinbefore shows that it likewise inhibits the secretion of ACTH and $\beta$-END-LI.

EXAMPLE XXX

The peptide [D-Tyr$^{12}$, Ala$^{19}$, Lys$^{23}$, Nle$^{24,38,40}$ Nva$^{27}$,]-hCRF(12-41) having the formula: H-D-Tyr-His-Leu-Leu-Arg-Glu-Val-Ala-Glu-Met-Ala-Lys-N le-Glu-Gln-Nva-Ala-Gln-Gln-Ala-His-Ser-Asn-Arg-Lys-L eu-Nle-Glu-Nle-Ile-NH$_2$ is synthesized. Testing in accordance with the general procedure set forth hereinbefore shows that it likewise inhibits the secretion of ACTH and $\beta$-END-LI.

EXAMPLE XXXI

The peptide [D-His$^{12}$, CMA$^{19,21,24,27}$, Tyr$^{32}$, Thr$^{33}$, Nle$^{38}$, Gln$^{40}$]-hCRF(11-41) having the formula: H-Thr-D-His-His-Leu-Leu-Arg-Glu-Val-CMA-Glu-CMA-Ala-A rg-CMA-Glu-Gln-CMA-Ala-Gln-Gln-Ala-Tyr-Thr-Asn-Arg-L Lys-Leu-Nle-Glu-Gln-Ile-NH$_2$ is synthesized. Testing in accordance with the general procedure set forth hereinbefore shows that it likewise inhibits the secretion of ACTH and $\beta$-END-LI.

EXAMPLE XXXII

The peptide [4Cl-D-Phe$^{12}$, Nle$^{19,27,38}$, D-Glu$^{20}$, Nva$^{21}$, Leu$^{24}$, Gly$^{40}$, CMA$^{41}$]-hCRF(12-41) having the formula: H-4Cl-D-Phe-His-Leu-Leu-Arg-Glu-Val-Nle-D-Glu-Nva-Ala-A rg-Leu-Glu-Gln-Nle-Ala-Gln-Gln-Ala-His-Ser-Asn-Arg-L ys-Leu-Nle-Glu-Gly-CMA-NH$_2$ is synthesized. Testing in accordance with the general procedure set forth hereinbefore shows that it likewise inhibits the secretion of ACTH and $\beta$-END-LI.

EXAMPLE XXXIII

The peptide [Benzoyl-D-Met$^{12}$, CML$^{21,24}$, Har$^{36}$, Nle$^{38}$, Leu$^{40}$, Phe$^{41}$]-hCRF(12-41) having the formula: Bz-D-Met-His-Leu-Leu-Arg-Glu-Val-Leu-Glu-CML-Ala-Arg-C ML-Glu-Gln-Leu-Ala-Gln-Gln-Ala-His-Ser-Asn-Arg-Har-L eu-Nle-Glu-Leu-Phe-NH$_2$ is synthesized. Testing in accordance with the general procedure set forth hereinbefore shows that it likewise inhibits the secretion of ACTH and $\beta$-END-LI.

EXAMPLE XXXIV

The peptide [D-His$^{12}$, Phe$^{21,24}$, Orn$^{23}$, Asp$^{27}$, Nle$^{38}$, CMA$^{40}$, Val$^{41}$]-hCRF(12-41) having the formula: H-D-His-His-Leu-Leu-Arg-Glu-Val-Leu-Glu-Phe-Ala-Orn-P he-Glu-Gln-Asp-Ala-Gln-Gln-Ala-His-Ser-Asn-Arg-Lys-L eu-Nle-Glu-CMA-Val-NH$_2$ is synthesized. Testing in accordance with the general procedure set forth hereinbefore shows that it likewise inhibits the secretion of ACTH and $\beta$-END-LI.

EXAMPLE XXXV

The peptide [formyl-D-Pal$^{12}$, Phe$^{19}$, Gln$^{21}$, Thr$^{22}$, Tyr$^{32}$, Nle$^{38}$, CML$^{40,41}$]-hCRF(12-41) having the formula: For-D-Pal-His-Leu-Leu-Arg-Glu-Val-Phe-G lu-Gln-Thr-Arg-Ala-Glu-Gln-Leu-Ala-Gln-Gln-Ala-Tyr-S er-Asn-Arg-Lys-Leu-Nle-Glu-CML-CML-NH$_2$ is synthesized. Testing in accordance with the general procedure set forth hereinbefore shows that it likewise inhibits the secretion of ACTH and $\beta$-END-LI.

EXAMPLE XXXVI

The peptide [D-Phe$^{12}$, Nle$^{21,38}$]-oCRF(12-41) having the formula: H-D-Phe-His-Leu-Leu-Arg-Glu-Val-Leu-Glu-Nle-Thr-Lys-A la-Asp-Gln-Leu-Ala-Gln-Gln-Ala-His-Ser-Asn-Arg-Lys-L eu-Nle-Asp-Ile-Ala-NH$_2$ is synthesized. Testing in accordance with the general procedure set forth hereinbefore shows that it likewise inhibits the secretion of ACTH and β-END-LI.

EXAMPLE XXXVII

The peptide [D-Phe$^{12}$, Nle$^{21,38}$, Arg$^{36}$]-oCRF (12-41) having the formula: H-D-Phe-His-Leu-Leu-Arg-Glu-Val-Leu-Glu-Nle-Thr-Lys-A la-Asp-Gln-Leu-Ala-Gln-Gln-Ala-His-Ser-Asn-Arg-Arg-L eu-Nle-Asp-Ile-Ala-NH$_2$ is synthesized. Testing in accordance with the general procedure set forth hereinbefore shows that it likewise inhibits the secretion of ACTH and β-END-LI.

EXAMPLE XXXVIII

The peptide [D-Phe$^{12}$, Nle$^{21,38}$, CML$^{37}$]-oCRF(12-41) having the formula: H-D-Phe-His-Leu-Leu-Arg-Glu-Val-Leu-Glu-Nle-Thr-Lys-A la-Asp-Gln-Leu-Ala-Gln-Gln-Ala-His-Ser-Asn-Arg-Lys-C ML-Nle-Asp-Ile-Ala-NH$_2$ is synthesized. Testing in accordance with the general procedure set forth hereinbefore shows that it likewise inhibits the secretion of ACTH and β-END-LI.

CRF profoundly stimulates the pituitary-adrenalcortical axis, and CRF antagonists should be useful to inhibit the functions of this axis in some types of patients with high ACTH and endogenous glucocorticoid production. For example, CRF antagonists may be useful in regulating pituitary-adrenal function in patients having pituitary Cushings disease or any CRF-sensitive tumor.

Most other regulatory peptides have been found to have effects upon the endocrine system, the central nervous system and upon the gastrointestinal tract. Because ACTH and β-END-LI secretion is the "sine qua non" of mammal's response to stress, it was not surprising that CRF has significant effects on the brain as a mediator of many of the body's stress responses. Accordingly, CRF antagonists delivered to the brain should also find application in modifying the mood, learning and behavior of normal and mentally disordered individuals. Furthermore, CRF antagonists in the brain could ameliorate stress-induced conditions to which endogenous CRF might contribute, including some types of hypertension, infertility, decreased libido, impotency and hyperglycemia. Because peripherally administered CRF antagonists reduce the levels of ACTH, β-END, β-lipotropin, other pro-opiomelanocortin gene products and corticosterone, administration of the antagonists may be used to reduce the effects of all of these substances on the brain to thereby influence memory, mood, pain appreciation, etc., and more specifically, alertness, depression and/or anxiety, as well as to modulate the immune system, gastrointestinal tract and adrenalcortical growth and function.

All CRF related peptides have been shown to dilate the mesenteric vascular bed. CRF antagonists may also be of use for decreasing blood flow to the gastrointestinal tract of mammals, particularly humans. Also, oCRF influences gastric acid production, and CRF antagonists are expected to also be effective to modulate gastrointestinal functions.

CRF antagonists or the nontoxic addition salts thereof, combined with a pharmaceutically or veterinarily acceptable carrier to form a pharmaceutical composition, may be administered to mammals, including humans, either intravenously, subcutaneously, intramuscularly, percutaneously, e.g. intranasally, intracerebroventricularly or orally. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans may be employed by a physician to inhibit endogenous gluco-corticoid production or for possible uses outlined above. The required dosage will vary with the particular condition being treated, with the severity of the condition and with the duration of desired treatment. In order to block the stress-related effects of endogenous CRF within the central nervous system, it may be necessary to deliver the CRF antagonists into the cerebral ventricle or spinal fluid. Alternatively, a means of modifying the antagonists so that they could penetrate the blood-brain barrier should be found.

These peptides may also be used to evaluate hypothalamic pituitary adrenal function in mammals with suspected endocrine or central nervous system pathology by suitable administration followed by monitoring body functions. For example, administration may be used as a diagnostic tool to evaluate the basis of Cushings disease.

Such peptides are often administered in the form of pharmaceutically or veterinarily acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically or veterinarily-acceptable carrier. Usually, the dosage will be from about 0.01 to about 10 milligrams of the peptide per kilogram of the body weight of the host animal. As used herein all temperatures are .C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at other positions in the CRF peptide chain can be made in accordance with present or future developments without detracting from the potency of the antagonists. For instance, instead of the simple amide at the C-terminal, a lower alkyl-substituted amide, e.g. 1-4 carbon atoms, i.e. methylamide, ethylamide, etc, may be incorporated. Such peptides are considered as being within the scope of the invention.

Various features of the invention are emphasized in the claims which follow.

What is claimed is:

1. A CRF antagonist peptide having one of the following formulae:

H-D-Phe-His-Leu-Leu-Arg-Glu-Val-Leu-Glu-$R_{21}$-Ala-Arg-Ala-Glu-Gln-Leu-Ala-Gln-Gln-Ala-His-Ser-Asn-Arg-$R_{36}$-$R_{37}$-$R_{38}$-Glu-Ile-Ile-$NH_2$, and H-D-Phe-His-Leu-Leu-Arg-Glu-Val-Leu-Glu-$R_{21}$-Thr-Lys-Ala-Asp-Gln-Leu-Ala-Gln-Gln-Ala-His-Ser-Asn-Arg-$R_{38}$-$R_{37}$-$R_{38}$-Asp-Ile-Ala-$NH_2$.

wherein $R_{21}$ is met or Nle, $R_{26}$ is Lys, Arg or Leu, $R_{37}$ is Leu or CML, and $R_{38}$ is Nle, or a non-toxic addition salt thereof.

2. A peptide in accordance with claim 1 wherein $R_{36}$ is Lys.

3. A peptide in accordance with claim 1 wherein $R_{37}$ is CML.

4. A peptide in accordance with claim 1 wherein $R_{21}$ is Nle.

5. A CRF antagonist peptide having the formula:

H-D-Phe-His-Leu-Leu-Arg-Glu-Val-Leu-Glu-Nle-Ala-Arg-Ala-Glu-Gln-Leu-Ala-Gln-Gln-Ala-His-Ser-Asn-Arg-$R_{36}$-$R_{37}$-Nle-Glu-Ile-Ile-$NH_2$, wherein $R_{36}$ is Lys or Arg and $R_{37}$ is Leu or CML.

6. A CRF antagonist peptide having the formula:

H-D-Phe-His-Leu-Leu-Arg-Glu-Val-Leu-Glu-Nle-Ala-Arg-Ala-Glu-Gln-Leu-Ala-Gln-Gln-Ala-His-Ser-Asn-Arg-Lys-CML-Nle-Glu-Ile-Ile-$NH_2$.

* * * * *

UNITED STATES PATENT AND TRADEMARK OFFICE
CERTIFICATE OF CORRECTION

PATENT NO. : 5,109,111
DATED : April 28, 1992
INVENTOR(S) : Rivier et al.

It is certified that error appears in the above-identified patent and that said Letters Patent is hereby corrected as shown below:

Column 1, line 35, "G In-" should be --Gln-Ala-His-Ser-Asn-Arg-Lys-Leu-Leu-Asp--. Column 1, line 66, "Ala" should be --ala--. Column 1, line 67, "H" should be --Y--. Column 2, line 10, "Ileu" should be --leu-- and "Nla" should be --ala--. Column 4, line 59, "y-carboxyl" should be --γ-carboxyl--. Column 8, line 6, "River" should be --Rivier--. Column 8, line 48, "1 0" should be --1.0--. Column 8, line 59, "(12-14)" should be (12-41)--. Column 9, line 27, "River" should be --Rivier--. Column 10, line 43, "β-residue" should be --30-residue--. Column 11, line 67, "Arg$^{37}$" should be --Arg$^{36}$--. Column 13, line 41, "N Nle" should be --Nle--. Column 15, lines 52-53, "L eu" should be --Leu-Leu---. Column 16, line 17, "L Lys" should be --Lys--. Column 18, line 49, ".C." should be --°C.--. Claim 1, column 19, line 9, "$R_{38}$-R $_{37}$" should be --$R_{36}$-$R_{37}$--. Claim 1, column 19, line 10, "met" should be --Met-- and "$R_{26}$" should be --$R_{36}$--. Claim 6, column 20, line 12, "a la" should be --Ala--.

Signed and Sealed this

Twenty-eighth Day of September, 1993

Attest:

BRUCE LEHMAN

Attesting Officer

Commissioner of Patents and Trademarks